(12) United States Patent
Rao et al.

(10) Patent No.: US 8,350,031 B2
(45) Date of Patent: Jan. 8, 2013

(54) PROCESSES FOR THE SYNTHESIS OF LEVOCETIRIZINE AND INTERMEDIATES FOR USE THEREIN

(75) Inventors: Dharmaraj Ramachandra Rao, Maharashtra (IN); Rajendra Narayanrao Kankan, Maharashtra (IN); Maruti Ghagare, Maharashtra (IN); Sandip Vasant Chikhalikar, Maharashtra (IN)

(73) Assignee: CIPLA Limited, Mumbai (IN)

( * ) Notice: Subject to any disclaimer, the term of this patent is extended or adjusted under 35 U.S.C. 154(b) by 0 days.

(21) Appl. No.: 12/993,011

(22) PCT Filed: Jun. 2, 2009

(86) PCT No.: PCT/GB2009/001385
§ 371 (c)(1),
(2), (4) Date: Feb. 8, 2011

(87) PCT Pub. No.: WO2009/147389
PCT Pub. Date: Dec. 10, 2009

(65) Prior Publication Data
US 2011/0184174 A1  Jul. 28, 2011

(30) Foreign Application Priority Data
Jun. 2, 2008  (IN) .................. 1173/MUM/2008

(51) Int. Cl.
*C07D 241/04* (2006.01)
(52) U.S. Cl. ........................................ 544/396
(58) Field of Classification Search .................. 544/396
See application file for complete search history.

(56) References Cited

U.S. PATENT DOCUMENTS

| 2,792,398 | A | * | 5/1957 | Kyrides ........................ 544/396 |
| 4,525,358 | A | | 6/1985 | Baltes et al. |
| 5,478,941 | A | | 12/1995 | Cossement et al. |

FOREIGN PATENT DOCUMENTS

| EP | 0058146 A1 | 8/1982 |
| EP | 0147085 B1 | 3/1990 |
| GB | 2225321 A | 5/1990 |
| WO | 2007066163 A2 | 6/2007 |
| WO | 2009147389 A2 | 12/2009 |
| WO | 2009147389 A3 | 12/2009 |
| WO | 2009147389 A8 | 12/2009 |

OTHER PUBLICATIONS

Foreign communication from the priority application—International Search Report and Written Opinion, PCT/GB2009/001385, May 19, 2010, 19 pages.
Wuts, Peter, G. M., et al., "Greene's Protective Groups in Organic Synthesis," Fourth Edition, 2006, pp. 814-819 plus cover and publication pages, John Wiley and Sons, Inc., XP002545586.
Foreign communication from the priority application—International Preliminary Report on Patentability, PCT/GB2009/001385, Dec. 6, 2010, 11 pages.

\* cited by examiner

*Primary Examiner* — Golam M M Shameem
*Assistant Examiner* — Karen Cheng
(74) *Attorney, Agent, or Firm* — Conley Rose, P.C.; Rodney B. Carroll

(57) ABSTRACT

The present invention provides a compound of formula (IV)

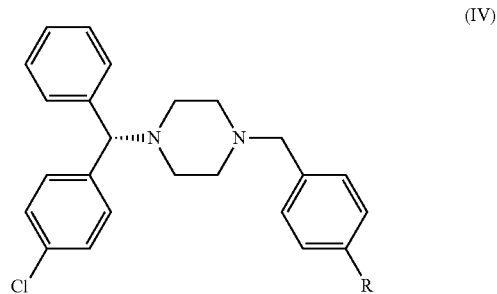

wherein R is Cl, Br, $NO_2$, OH or OR', and R' is alkyl, and its use in the synthesis of levocetirizine, including its use in the synthesis of (−)-1-[(4-chlorophenyl)-phenylmethyl]piperazine, an intermediate useful in the synthesis of levocetirizine. The present invention also provides compounds (II) and (III) which are useful in the synthesis of compound (IV).

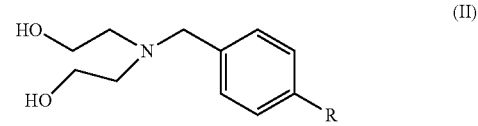

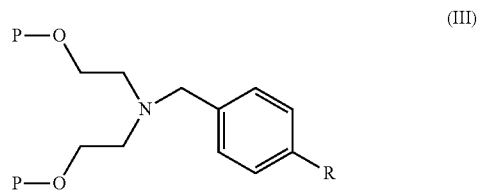

23 Claims, No Drawings

PROCESSES FOR THE SYNTHESIS OF LEVOCETIRIZINE AND INTERMEDIATES FOR USE THEREIN

CROSS-REFERENCE TO RELATED APPLICATIONS

This application is a filing under 35 U.S.C. 371 of International Application No. PCT/GB2009/001385 filed Jun. 2, 2009, entitled "Processes for the Synthesis of Levocetirizine and Intermediates for Use Therein," claiming priority of Indian Patent Application No. 1173/MUM/2008 filed Jun. 2, 2008, which applications are incorporated by reference herein in their entirety.

FIELD OF INVENTION

The present invention relates to a process for the preparation of (−)-1-[(4-chlorophenyl)-phenylmethyl]piperazine (I), a key intermediate for the synthesis of levocetirizine, and novel intermediates for use in the process.

BACKGROUND OF THE INVENTION

Cetirizine, chemically [2-[4-[(4-chlorophenyl)phenylmethyl]-1-piperazinyl]ethoxy]acetic acid is an antihistamine non-sedating type histamine $H_1$-receptor antagonist, indicated for relief of symptoms associated with seasonal allergic rhinitis, perennial allergic rhinitis and related diseases.

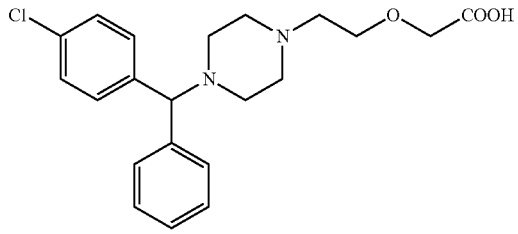

Cetirizine

U.S. Pat. No. 4,525,358 and its equivalent EP 58146 disclose cetirizine and its pharmaceutically acceptable salts. The process for the synthesis of cetirizine comprises condensation of 1-[(4-chlorophenyl)-phenylmethyl]piperazine with 2-chloroethoxy acetamide to obtain 2-[2-[4-[(4-chlorophenyl)phenylmethyl]-1-piperazinyl]-ethoxy acetamide which on hydrolysis gives cetirizine.

It was found later that the pharmacological activity resides primarily in (R)-isomer or (−) form known as levocetirizine. GB 2225321 describes a process for the preparation of the dextro and levorotatory isomers of cetirizine comprising hydrolysis of 2-[2-[4-[(4-chlorophenyl)phenylmethyl]-1-piperazinyl]-ethoxy acetonitrile.

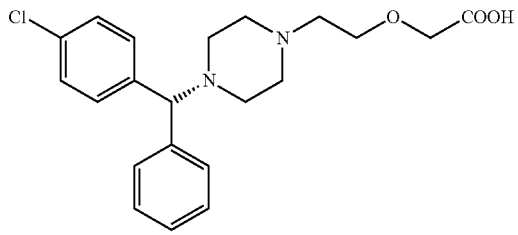

Levocetirizine (−)-1-[(4-chlorophenyl)-phenylmethyl]piperazine is a very important intermediate in the synthesis of levocetirizine.

U.S. Pat. No. 5,478,941 discloses a process for the synthesis of (−)-1-[(4-chlorophenyl)-phenylmethyl]piperazine involving hydrolyzing 1-[(4-chlorophenyl)-phenylmethyl]-4-(4-methylphenyl)sulfonyl piperazine with hydrobromic acid in the presence of 4-hydroxybenzoic acid.

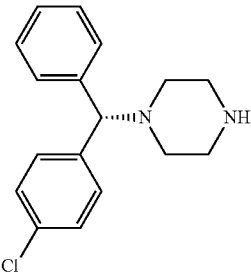

(I)

The alternative routes of synthesis of (−)-1-[(4-chlorophenyl)-phenylmethyl]piperazine disclosed in the prior art involve the use of bis chloro ethylamine which is carcinogenic in nature.

Levocetirizine is a highly-potent non-sedating anti-allergic agent. Hence, there are continuous attempts to develop new processes for the synthesis of levocetirizine and its intermediates. The present invention describes a new process for the preparation of the key intermediate (−)-1-[(4-chlorophenyl)-phenylmethyl]piperazine.

OBJECT OF THE INVENTION

It is an object of the present invention to provide a process for the preparation of (−)-1-[(4-chlorophenyl)-phenyl methyl]piperazine (I), a key intermediate for use in the synthesis of levocetirizine or its salts.

It is another object of the present invention to provide novel intermediates useful in the synthesis of levocetirizine.

It is yet another object of the present invention to provide processes for the preparation of the novel intermediates useful in the synthesis of levocetirizine.

SUMMARY OF THE INVENTION

According to a first aspect of the present invention, there is provided a compound of formula (IV)

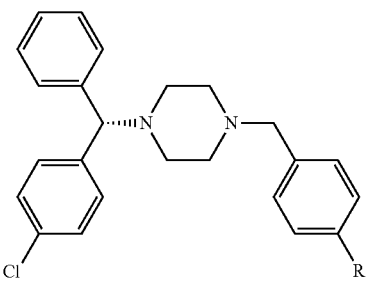

(IV)

wherein R is selected from Cl, Br, $NO_2$, OH or OR', and R' is alkyl. In an embodiment, R' is a straight- or branched-chain $C_1$ to $C_6$ alkyl such as methyl, ethyl, n-propyl, i-propyl, n-butyl, pentyl or hexyl. Preferably, R is OR'. More preferably, R is OMe, i.e., methoxy.

According to another aspect of the present invention, there is provided a process for preparing a compound of formula (IV) which process comprises reacting a compound of formula (III) with (−)-(4-chlorophenyl)phenylmethyl amine in the presence of a base and a solvent

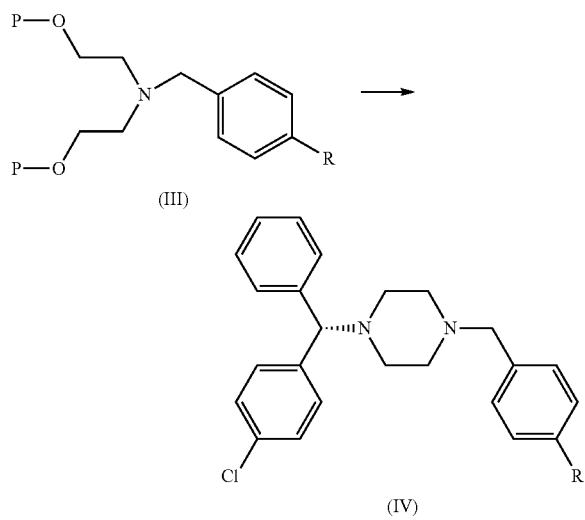

wherein R is Cl, Br, NO$_2$, OH or OR', and R' is alkyl, and wherein P is a protecting group. In an embodiment, R' is a straight- or branched-chain C$_1$ to C$_6$ alkyl such as methyl, ethyl, n-propyl, i-propyl, n-butyl, pentyl or hexyl. Preferably, R is OR'. More preferably, R is OMe, i.e., methoxy.

The base used for the reaction may be an organic or an inorganic base. The inorganic base may be potassium carbonate. The organic base may be selected from pyridine, triethyl amine or N,N-diisopropylethyl amine. Most preferably, the base used is N-ethyldiisopropylamine.

The solvent may be selected from toluene, dimethylsulfoxide, N,N-dimethylformamide, acetonitrile, hexamethyl phosphoramide, N-methyl pyrrolidine, dimethylacetamide, dioxane, sulfolane, tetrahydrofuran, most preferably dimethylsulfoxide or a mixture of solvents such as a mixture of N,N-dimethylformamide and acetonitrile or N,N-dimethylformamide and dimethylsulfoxide, dimethylsulfoxide and acetonitrile.

The protecting group may be selected from mesylate, besylate, tetrabutyl dimethyl silyl, dimethoxy trityl, tetra isopropyl silyl and tetrahydropyranyl. The protecting groups are derived from the following protecting agents: methane sulfonyl chloride, benzene sulfonic acid, tetrabutyl dimethyl silane, dimethoxy trityl chloride, tetra isopropyl silyl chloride, and tetrahydropyran, respectively.

In a preferred embodiment, compound (III) has the following structure (IIIa), i.e., the protecting group is mesylate.

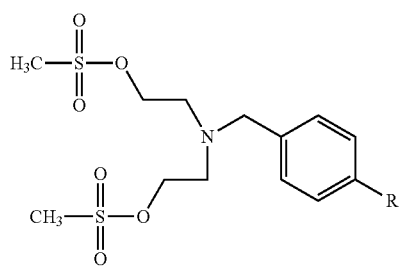

The process may further comprise purifying compound (IV). The purification may involve converting compound (IV) to a salt thereof by treatment with an acid such as oxalic acid or hydrochloric acid (gas) in the presence of solvent such as acetone or ethyl acetate or methanol, reacting the salt with a basic solution and isolating compound (IV).

The basic solution may be a sodium hydroxide solution, which is used to adjust the pH of the reaction mass to 13-14. The product may be extracted using a suitable solvent to isolate purified compound (IV). The extracting solvent may be selected from dichloromethane, ethyl acetate or toluene preferably, dichloromethane.

The conversion of compound (IV) to a salt thereof is an effective optional method for eliminating the impurities formed during the reaction.

Compound (IV) as prepared above may be used in any one of the processes described below for producing compound (I).

According to another aspect of the present invention, there is provided a process for preparing levocetirizine or a pharmaceutically acceptable salt thereof, the process comprising converting compound (IV) to levocetirizine. The conversion may be according to any one of the processes described below.

According to a further aspect of the present invention, there is provided a compound of formula (III)

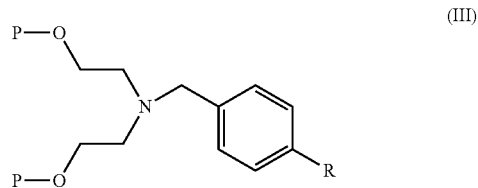

wherein R is Cl, Br, NO$_2$, OH or OR', and R' is alkyl, and wherein P is a protecting group.

In an embodiment, R' is a straight- or branched-chain C$_1$ to C$_6$ alkyl such as methyl, ethyl, n-propyl, i-propyl, n-butyl, pentyl or hexyl. Preferably, R is OR'. More preferably, R is OMe, i.e., methoxy.

The protecting group may be selected from mesylate, besylate, tetrabutyl dimethyl silyl, dimethoxy trityl, tetra isopropyl silyl and tetrahydropyranyl. Preferably, the protecting group is mesylate.

Compound (III) for use in the above process may be prepared according to the process described below.

According to another aspect of the present invention, there is provided a process for preparing a compound of formula (III) comprising reacting a compound of formula (II) with a protecting agent in the presence of a solvent and a base

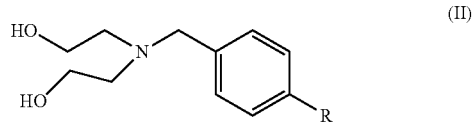

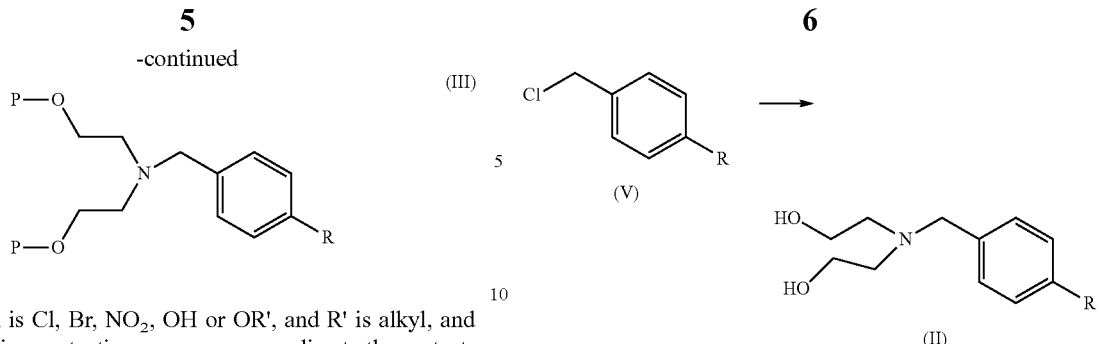

(III)

wherein R is Cl, Br, NO₂, OH or OR', and R' is alkyl, and wherein P is a protecting group corresponding to the protecting agent. In an embodiment, R' is a straight- or branched-chain $C_1$ to $C_6$ alkyl such as methyl, ethyl, n-propyl, i-propyl, n-butyl, pentyl or hexyl. Preferably, R is OR'. More preferably, R is OMe, i.e., methoxy.

The suitable protecting agent may be selected from methane sulfonyl chloride, benzene sulfonic acid, tetrabutyl dimethyl silane, dimethoxy trityl chloride, tetra isopropyl silyl chloride, and tetrahydropyran, most preferably methane sulfonyl chloride.

The base used may be an organic or inorganic base. The inorganic base may be selected from potassium tertbutoxide, potassium carbonate, sodium methoxide, potassium methoxide and sodium carbonate. The organic base may be selected from pyridine, triethyl amine and N,N-diisopropylethyl amine, most preferably triethylamine.

The solvent may be dichloromethane, acetonitrile, tetrahydrofuran, ethyl acetate or toluene, most preferably dichloromethane.

Compound (III) as prepared above may be used in any one of the processes described above for producing compound (IV).

According to another aspect of the present invention, there is provided a process for preparing levocetirizine or a pharmaceutically acceptable salt thereof, the process comprising converting compound (III) to levocetirizine. The conversion may be according to any one of the processes described below.

Compound (II) for use in the above process may be prepared according to the process described below.

According to a further aspect of the present invention, there is provided a compound of formula (II)

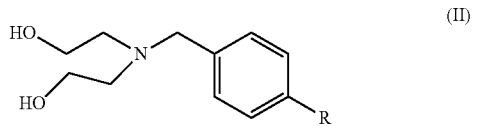

(II)

wherein R is Cl, Br, NO₂, OH or OR', and R' is alkyl. In an embodiment, R' is a straight- or branched-chain $C_1$ to $C_6$ alkyl such as methyl, ethyl, n-propyl, i-propyl, n-butyl, pentyl or hexyl. Preferably, R is OR'. More preferably, R is OMe, i.e., methoxy.

According to another aspect of the present invention, there is provided a process for preparing a compound of formula (II) which comprises condensation of diethanolamine and a benzyl chloride (V) in the presence of a base and a solvent (V)

(II)

wherein R is Cl, Br, NO₂, OH or OR', and R' is alkyl. In an embodiment, R' is a straight- or branched-chain $C_1$ to $C_6$ alkyl such as methyl, ethyl, n-propyl, i-propyl, n-butyl, pentyl or hexyl. Preferably, R is OR'. More preferably, R is OMe, i.e., methoxy.

The base used may be an organic or inorganic base. The inorganic base may be selected from potassium tertbutoxide, potassium carbonate, sodium methoxide, potassium methoxide and sodium carbonate. The organic base may be selected from pyridine, triethyl amine and N,N-diisopropylethyl amine, most preferably triethylamine.

A suitable solvent may be dichloromethane, ethyl acetate, toluene, acetone, acetonitrile, tetrahydrofuran, methanol, most preferably dichloromethane.

Compound (II) as prepared above may be used in any one of the processes described above for producing compound (III).

According to another aspect of the present invention, there is provided a process for preparing levocetirizine or a pharmaceutically acceptable salt thereof, the process comprising converting compound (IV) to levocetirizine. The conversion may be according to any one of the processes described below.

According to another aspect of the present invention, there is provided a process for preparing a compound of formula (I) comprising converting a compound of formula (IV) to the compound (I).

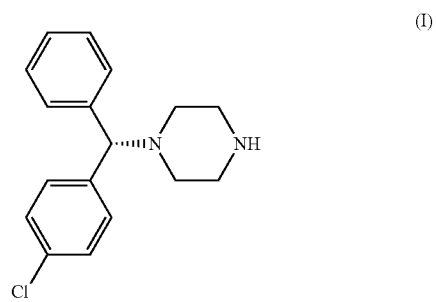 [SMILES: Clc1ccc([C@H](c2ccccc2)N2CCNCC2)cc1]

(I)

The conversion of compound (IV) to compound (I) may comprise reacting the compound (IV) with a deprotecting agent to obtain the corresponding carbamate ester of (−)-1-[(4-chlorophenyl)-phenylmethyl] piperazine, and hydrolysing the carbamate ester to obtain the compound (I).

In an embodiment, the deprotecting agent is selected from ethyl chloroformate, 1-chloroethyl chloroformate, vinyl chloroformate, phenyl chloroformate, 2,2,2-trichloroethyl chloroformate, 4-chlorophenyl chlorothionoformate, 2,4,6-tribromophenyl chlorothionoformate, triphosgene and cyanogen bromide.

The deprotection is preferably carried out at the reflux temperature of the solvent.

Suitably, the hydrolysis is carried out using methanol.

According to another aspect of the present invention, there is provided a process for the preparation of levocetirizine or a salt thereof, which comprises conversion of a compound of formula (IV) to levocetirizine, and optionally converting the levocetirizine to the salt thereof.

In an embodiment, the conversion comprises preparing a compound of formula (I) from the compound of formula (IV) as described above, and converting the compound (I) to levocetirizine.

In an embodiment, the conversion of compound (I) to levocetirizine comprises reacting compound (I) with a 2-chloroethoxy acetic acid derivative in the presence of a base and a solvent to obtain the corresponding [2-[4-[(4-chlorophenyl)phenylmethyl]-1-piperazin-1-yl]ethoxy]acetic acid derivative, and hydrolyzing the acetic acid derivative to obtain levocetirizine.

In an embodiment, the 2-chloroethoxy acetic acid derivative is 2-chloroethoxy acetamide, 2-chloroethoxy acetate or 2-chloroethoxy acetonitrile.

The base may be sodium carbonate or potassium carbonate. The solvent may be toluene or xylene.

In an embodiment, the hydrolysis is carried out using sodium hydroxide.

In a preferred embodiment, there is provided a process for preparing levocetirizine comprising:

i) condensation of diethanolamine and a benzyl chloride (V) in the presence of dichloromethane and triethylamine to obtain a compound of formula (II);

ii) reacting the compound (II) with methane sulphonyl chloride in the presence of dichloromethane and triethylamine to obtain a compound of formula (III);

iii) reacting the compound (III) with (−)-(4-chlorophenyl) phenylmethyl amine in the presence of N-ethyldiisopropylamine and N,N-dimethylsulfoxide to obtain a compound of formula (IV);

iv) reacting the compound (IV) with 1-chloroethyl chloroformate to obtain corresponding carbamate ester of (−)-1-[(4-chlorophenyl)-phenyl methyl]piperazine which is hydrolyzed using methanol to obtain a compound of formula (I); and v) treating compound (I) with 2-chloroethoxy acetamide in the presence of potassium carbonate and toluene to obtain [2-[4-[(4-chlorophenyl)phenylmethyl]-1-piperazinyl] ethoxy]acetamide which is hydrolyzed using sodium hydroxide to obtain levocetirizine.

The novel compounds of formula (II), (III) and (IV) are useful in novel processes for the preparation of levocetirizine. The processes do not involve use of bis-chloro ethylamine as the precursor which is carcinogenic. The novel intermediates are simple and safe to use. Hence, the processes and compounds of the present invention are advantageous.

DETAILED DESCRIPTION OF THE INVENTION

The present invention provides a process for the synthesis of (−)-1-[(4-chlorophenyl)-phenylmethyl]piperazine (I) which is a key intermediate in the synthesis of levocetirizine.

The process is simple, safe, ecofriendly and gives good yield and purity of levocetirizine.

In an embodiment, the present invention provides a process for the synthesis of compound (I) which may comprise the use of novel intermediates (II), (III) and (IV).

In an embodiment, there is provided a novel compound of formula (IV)

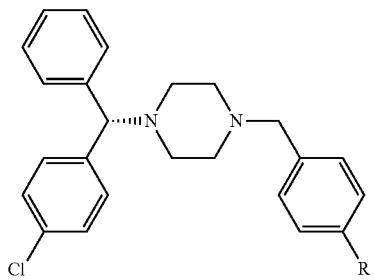

wherein R is selected from Cl, Br, $NO_2$, OH or OR' (R'=alkyl).

In another embodiment of the present invention, there is provided a process for preparation of levocetirizine comprising reacting compound (IV) with a deprotecting agent to obtain the corresponding carbamate ester of (−)-1-[(4-chlorophenyl)-phenyl methyl]piperazine which is hydrolyzed, for example using methanol, to obtain a compound of formula (I). The compound (I) is further treated with a 2-chloroethoxy acetic acid derivative such as 2-chloroethoxy acetamide or 2-chloroethoxy acetate or 2-chloroethoxy acetonitrile in the presence of a base and a solvent to obtain the corresponding [2-[4-[(4-chlorophenyl)phenylmethyl]-1-piperazinyl] ethoxy]acetic acid derivative which is hydrolyzed, for example, using sodium hydroxide, to obtain levocetirizine.

The deprotecting agent may be selected from ethyl chloroformate, 1-chloroethyl chloroformate, vinyl chloroformate, phenyl chloroformate, 2,2,2-trichloroethyl chloroformate, 4-chlorophenyl chlorothionoformate, 2,4,6-tribromophenyl chlorothionoformate, triphosgene and cyanogen bromide. The most preferred deprotecting agent is 1-chloroethyl chloroformate.

The solvent may be selected from 1,2-dichloroethane, tetrahydrofuran, toluene, dichloromethane or acetonitrile or a mixture of toluene and dichloromethane (1:1). The preferred solvent is tetrahydrofuran.

The deprotection may be carried out by heating the reaction mass at the reflux temperature of the solvent.

The hydrolysis may be carried out by reaction of the carbamate ester (−)-1-[(4-chlorophenyl)-phenylmethyl]piperazine with an alcohol, preferably methanol.

The carbamate ester may be heated at the reflux temperature of the solvent and concentrated to obtain a residue. The residue may be treated with aqueous HCl and washed with dichloromethane whereby the layers are separated. The aqueous layer may be treated with a basic solution, such as a sodium hydroxide solution, and extracted, for example, with dichloromethane. The separated organic layer is concentrated to obtain compound (I).

Optionally, compound (I) can be purified, for example, by recrystallization. The recrystallization may involve converting compound (I) to a salt thereof by treating compound (I) with an acid such as hydrochloric acid or oxalic acid in the presence of a solvent. The reaction mass may be heated at the reflux temperature of the solvent and the salt isolated, for example, by filtration and drying. The salt may be treated with a basic solution such as sodium hydroxide solution to adjust the pH of the reaction mixture to 13-14, followed by heating to about 50-55° C. After cooling, the resulting product is isolated, for example, by filtration and drying under vacuum, to obtain purified compound (I).

Optionally, compound (I) can be recrystallized by treating with heptane and adjusting the pH of the solution to 13-14 using a basic solution such as sodium hydroxide solution. The solution may be stirred at a temperature ranging from 25 to 30° C. for about 15 hours whereby compound (I) is obtained.

The compound (I) may be further treated with a 2-chloroethoxy acetic acid derivative such as 2-chloroethoxy acetamide or 2-chloroethoxy acetate or 2-chloroethoxy acetonitrile in the presence of a base such as sodium carbonate or potassium carbonate, and a solvent such as toluene or xylene to obtain the corresponding [2-[4-[(4-chlorophenyl)phenylmethyl]-1-piperazinyl]ethoxy]acetic acid derivative which on hydrolysis, for example, using sodium hydroxide gives levocetirizine.

According to another aspect of the present invention, there is provided a process for preparing a novel compound of formula (IV) which comprises reacting compound (III) with (−)-(4-chlorophenyl)phenylmethyl amine in the presence of a base and a solvent.

In another preferred embodiment, compound (III) is compound (IIIa) i.e., the protecting group is mesylate.

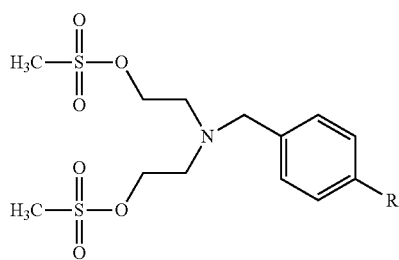
(IIIa)

The base used for the reaction may be an organic or inorganic base. The inorganic base may be selected from potassium carbonate. The organic base may be selected from pyridine, triethyl amine or N,N-diisopropylethyl amine. Most preferably, the base used is N-ethyldiisopropylamine.

The solvent may be selected from toluene, dimethylsulfoxide, N,N-dimethylformamide, acetonitrile, hexamethyl, phosphoramide, N-methyl pyrrolidine, dimethylacetamide, dioxane, sulfolane, tetrahydrofuran, most preferably dimethylsulfoxide.

The solvent mixture may be a mixture of N,N-dimethylformamide and acetonitrile or N,N-dimethylformamide and dimethylsulfoxide, dimethylsulfoxide and acetonitrile.

Optionally, the compound of formula (IV) may be converted to its salt by treating with an acid such as oxalic acid or hydrochloric acid (gas) in presence of solvent such as acetone or ethyl acetate or methanol.

The reaction mass is heated at the reflux temperature of the solvent or solvent mixture.

The salt of compound of formula (IV) is treated with sodium hydroxide solution to adjust the pH of the reaction mass to 13-14. The product is extracted using a suitable solvent to isolate pure compound of formula (IV). The extracting solvent is selected from dichloromethane, ethyl acetate or toluene preferably, dichloromethane.

In yet another embodiment, there is provided a compound of formula (III)

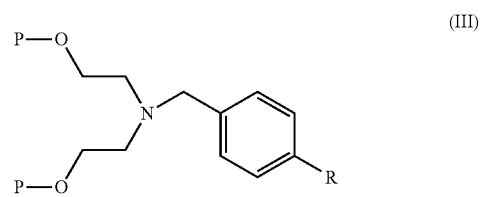
(III)

wherein R is Cl, Br, $NO_2$, OH or OR', and R' is alkyl, and wherein P is a protecting group.

In an embodiment, R' is a straight- or branched-chain $C_1$ to $C_6$ alkyl such as methyl, ethyl, n-propyl, i-propyl, n-butyl, pentyl or hexyl. Preferably, R is OR'. More preferably, R is OMe, i.e., methoxy.

The protecting agent may be selected from methane sulfonyl chloride, benzene sulfonic acid, tetrabutyl dimethyl silane, dimethoxy trityl chloride, tetra isopropyl silyl chloride and tetrahydropyran. Preferably, the protecting group is mesylate.

In an embodiment, the present invention provides a process for preparing a compound of formula (III) comprising reacting a compound of formula (II) with a suitable protecting agent in the presence of a suitable solvent and a base.

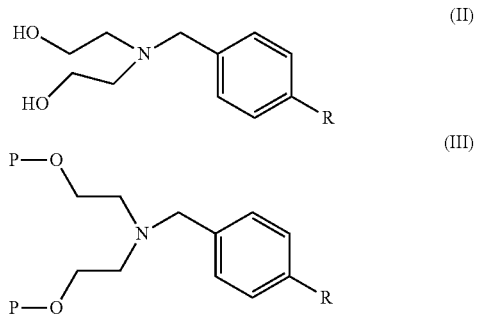

wherein R is Cl, Br, $NO_2$, OH or OR', and R' is alkyl, and wherein P is a protecting group corresponding to the protecting agent. In an embodiment, R' is a straight- or branched-chain $C_1$ to $C_6$ alkyl such as methyl, ethyl, n-propyl, i-propyl, n-butyl, pentyl or hexyl. Preferably, R is OR'. More preferably, R is OMe, i.e., methoxy.

The reaction of compound (II) with the protecting agent is carried out in presence of a base. The base used may be an organic or inorganic base. The inorganic base may be selected from potassium tertbutoxide, potassium carbonate, sodium methoxide, potassium methoxide, sodium carbonate and the like. The organic base may be selected from pyridine, triethyl amine, N,N-diisopropylethyl amine, most preferably triethylamine.

The solvent may be selected from dichloromethane, acetonitrile, tetrahydrofuran, ethyl acetate or toluene. Most preferable solvent being dichloromethane.

The suitable protecting agent can be selected from methane sulfonyl chloride, benzene sulfonic acid, tetrabutyl dimethyl silane, dimethoxy trityl chloride, tetra isopropyl silyl chloride, tetrahydropyran, most preferably methane sulfonyl chloride.

The protecting agent used is as a solution in a suitable solvent such as dichloromethane.

The reaction of compound of formula (II) with a protecting agent is carried out at a temperature ranging from −5 to −10° C.

After completion of the reaction, the mixture is washed with water whereby the layers get separated. The organic layer is collected and concentrated to obtain compound (III).

In another embodiment, there is provided a compound of formula (II)

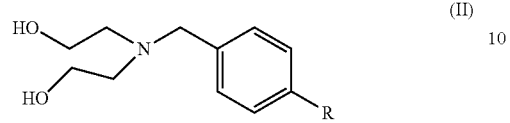

(II)

wherein R is the same as defined hereinbefore.

In an embodiment of the present invention, there is provided a process for preparing compound of formula (II) which comprises condensation of diethanolamine and p-substituted benzyl chloride in presence of a base and a solvent.

Preferably, the substitution of benzyl chloride which used for condensation is at para-position and can be selected from halogen such as chloro, bromo or alkoxy or nitro or ether or hydroxy, preferably an alkoxy group and most preferably a methoxy group.

The base used may be an organic or inorganic base. The inorganic base may be selected from potassium tertbutoxide, potassium carbonate, sodium methoxide, potassium methoxide, sodium carbonate and the like. The organic base may be selected from pyridine, triethyl amine, N,N-diisopropylethyl amine, most preferably triethylamine.

The suitable solvent used for the condensation may be dichloromethane, ethyl acetate, toluene, acetone, acetonitrile, tetrahydrofuran, methanol, most preferably dichloromethane.

The condensation is carried out below temperature of 5° C., preferably in the range of 0-5° C.

According to yet another aspect of the present invention, there is provided a process for preparing levocetirizine comprising:

i) condensation of diethanolamine and p-substituted benzyl chloride in presence dichloromethane and triethylamine to obtain compound of formula (II);

ii) reacting compound of formula (II) with methane sulphonyl chloride in presence of dichloromethane and triethylamine to obtain compound of formula (III);

iii) reacting compound (III) with (−)(4-chlorophenyl)phenylmethyl amine in presence of N-ethyldiisopropylamine and N,N-dimethylsulfoxide to obtain compound (IV);

iv) reacting compound (IV) with 1-chloroethyl chloroformate to obtain corresponding carbamate ester of (−)-1-[(4-chlorophenyl)-phenylmethyl]piperazine which is hydrolyzed using methanol to obtain compound of formula (I); and v) treating compound (I) with 2-chloroethoxy acetamide in presence of potassium carbonate and toluene to obtain [2-[4-[(4-chlorophenyl)phenyl methyl]-1-piperazinyl]ethoxy]acetamide which is hydrolyzed using sodium hydroxide to obtain Levocetirizine.

The reaction scheme is represented as follows:

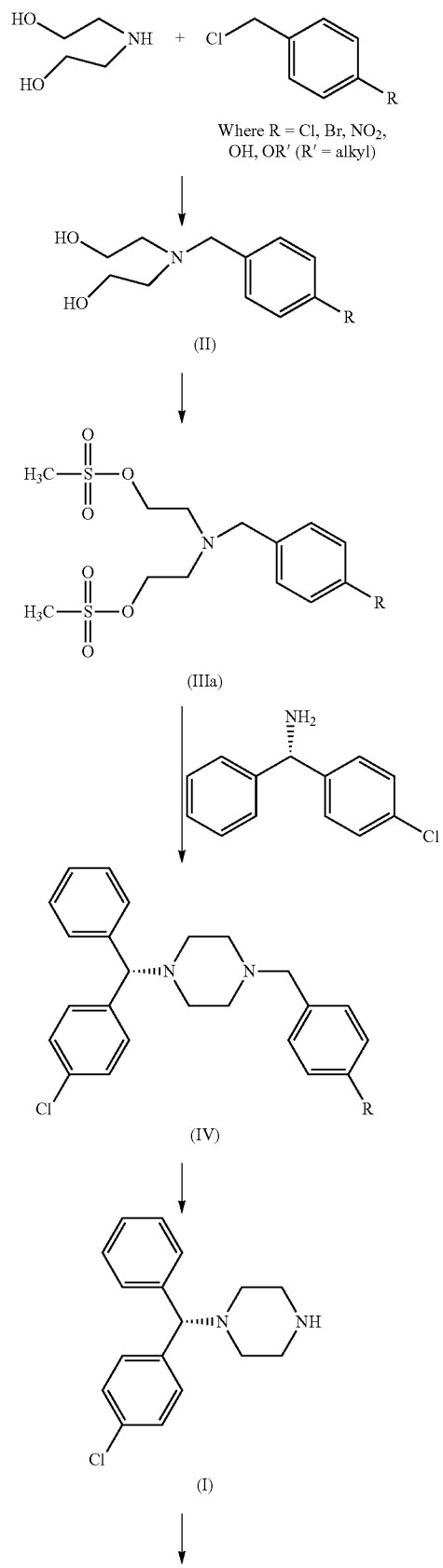

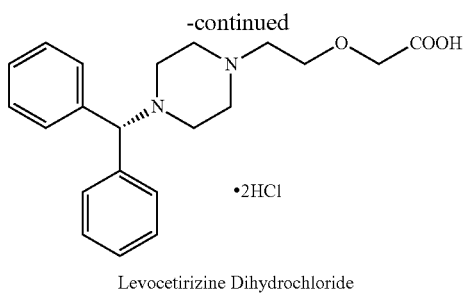

Levocetirizine Dihydrochloride

The process of the present invention is advantageous over the prior art as it avoids the use of bis chloro ethylamine which is carcinogenic in nature. One of the processes of the present invention comprises reaction of diethanol amine with para-substituted benzyl chloride. This para-substitution helps deprotection of compounds of formula (III) and (IV) to take place under mild reaction conditions. Hence, the process of the present invention is simple and safe.

EXAMPLES

There follow, by way of non-restrictive explanation of the present invention, the following examples.

Example 1

Preparation of 2-[(2-Hydroxy-ethyl)-(4-methoxy-benzyl)-amino]-ethanol 25 gms (0.2380 moles) of diethanolamine and 60 ml (0.4312 moles) triethylamine in 75 ml dichloromethane were taken in a reaction vessel and cooled to 0-5° C. with stirring. 40 gms (0.2554 moles) of p-methoxy benzyl chloride in 50 ml of dichloromethane was added thereto slowly. Further, the reaction mass was stirred with dichloromethane and maintained at a temperature of 25-30° C. for about 16 hours. The resulting solution was concentrated to get a residue. 200 ml of acetone was added to the residue, cooled to 0-5° C. for about one hour and filtered. The filtrate was concentrated to obtain the title compound as an oil (50.8 gms).

Example 2

Preparation of Methanesulfonic acid 2-[(2-methane-sulfonyloxy-ethyl)-(4-methoxy-benzyl)-amino]-ethyl ester 25 gms (0.1111 moles) of the product obtained from Example 1 and 45 gms (0.4455 moles) of triethylamine with 125 ml of dichloromethane were charged in a reaction vessel and cooled to −5 to −10° C. A solution of Methane sulphonyl chloride (45 gms, 0.3888 moles) in dichloromethane (50 ml) was added slowly at −5 to 10° C. and stirred for about 16 hours at 25-30° C. The resulting mixture was washed with water (25 ml). The collected organic layer was concentrated to obtain the title compound (36 gms).

Example 3

Preparation of (−)1-[(4-Chloro-phenyl)-phenyl-methyl]-4-(4-methoxy-benzyl)piperazine i) 7 gms (0.03218 moles) of (−)-(4-chlorophenyl)phenyl-methylamine and 10 gms (0.02624 moles) of compound prepared in Example 2 are mixed with 14 ml dimethylsulfoxide and 14 gms (0.1083 moles) N-ethyldiisopropylamine. The mixture was then heated at 90° C. for about four hours and then cooled. The reaction mass was quenched in water and extracted with dichloromethane. The collected organic layer was concentrated to get a residue (13 gms).

ii) To the residue obtained in step i) 130 ml of ethyl acetate and 14 gms (0.1111 moles) of oxalic acid dihydrate was added. The mixture was heated to obtain a clear solution and cooled to get oxalate salt of (−)1-[(4-Chloro-phenyl)-phenyl-methyl]-4-(4-methoxy-benzyl)piperazine. The salt was filtered and dried at 55° C. under vacuum (15 gms).

iii) The oxalate salt was further was treated with sodium hydroxide solution to pH of 9-10 and then extracted with ethyl acetate (3×25 ml). The collected organic layer was concentrated to obtain the title compound (9.2 gms).

Example 4

Preparation of (−)1-[(4-chloro-phenyl)-phenyl-methyl]-4-(4-methoxy-benzyl)piperazine i) To the residue obtained in step i) of Example 3, 130 ml acetone was added and cooled to 15-20° C. The pH of the reaction mass was adjusted to 1-2 by purging HCl gas. The reaction mixture was stirred for about one hour, heated to 50-55° C. for about one hour and then gradually cooled to 25-30° C. to obtain the dihydrochloride salt of (−)1-[(4-Chloro-phenyl)-phenyl-methyl]-4-(4-methoxy-benzyl)piperazine. The salt was filtered and dried at 55° C. under vacuum (15 gms).

ii) The salt obtained from step i) was treated with sodium hydroxide solution to pH of 9-10 and then extracted with (3×25 ml) of dichloromethane. The collected organic layer was concentrated to obtain the title compound (9.2 gms).

Example 5

Preparation of (−)-1-[(4-chloro-phenyl)-phenyl-methyl]-piperazine i) 35 ml tetrahydrofuran was added to 10 gms (0.02463 moles) of compound obtained from Example 3 followed by slow addition of 4 gms (0.02797 moles) 1-chloroethyl chloroformate in 10 ml of tetrahydrofuran. The reaction mass was heated at reflux temperature for about 3 hours and concentrated to an oil. To the oil 50 ml of methanol was added, heated to reflux for about 16 hours and concentrated to get a residue. The residue was further treated with 50 ml of aqueous HCl and washed with dichloromethane (3×30 ml). The aqueous layer was treated with sodium hydroxide solution and extracted with dichloromethane (50 ml). The organic layer was collected and concentrated to get an oil (5.7 gms).

ii) The product obtained from step i) was treated with 57 ml of ethyl acetate and 5.7 gms of oxalic acid was added thereto. The reaction mass was heated at the reflux temperature for about one hour, gradually cooled to 25-30° C. and stirred for about 2 hours. After completion of the reaction the resulting oxalate salt was filtered and dried at 55° C. under vacuum (9 gms).

iii) The salt obtained from step ii) was treated with 100 ml of water and 2.7 ml of heptane. The pH of the reaction mass was adjusted to 13-14 using 10% sodium hydroxide solution and stirred for about 1 hour. The reaction mass was heated at 50-55° C. for about one hour, gradually cooled to 25-30° C.

and stirred for about four hours. The resulting product was filtered, washed with water and dried under vacuum to obtain the title compound (4.5 gms).

Example 6

Preparation of (−)-1-[(4-Chloro-phenyl)-phenyl-methyl]-piperazine 35 ml tetrahydrofuran was added to 10 gms (0.02463 moles) of compound obtained from Example 3 followed by slow addition of 4 gms (0.02797 moles) 1-chloroethyl chloroformate in 10 ml of tetrahydrofuran. The reaction mass was heated at reflux temperature for about 3 hours and concentrated to an oil. To the oil 50 ml of methanol was added, heated to reflux for about 16 hours and concentrated to get a residue. The residue was further treated with 50 ml of aqueous HCl and washed with dichloromethane (3×30 ml). To the aqueous layer 2 ml of n-Heptane was added and then treated with sodium hydroxide solution at 25-30° C. The reaction mass was stirred at 25-30° C. for about 12 hours. After completion of the reaction the product obtained was filtered and dried under vacuum at 50-55° C. to obtain the title compound (4.5 gms).

Example 7

Preparation of Levocetirizine dihydrochloride i) 8 gms of product of Example 5 or 6 were dissolved in 48 ml of toluene. 5.8 gms (0.04233 moles) of 2-chloroethoxy acetamide was added along with 5 gms (0.03623 moles) of potassium carbonate, 0.4 gm (0.002440 moles) of potassium iodide and 8 ml of dimethylformamide at 25-30° C. The reaction mass was heated at 105-110° C. to remove water azeotropically. The heating was continued till completion of the reaction. The mixture was cooled to 50° C. and 64 ml of acetone, 12 gms of hyflo was added thereto. The mixture was further cooled to 10-15° C., maintained for about 1 hour and then filtered. Washings were given with acetone till colorless filtrate was obtained. Further, 32 ml of acetone was added to the filtrate and cooled to 10-15° C. To this 11 ml of IPA-HCl was added slowly so that pH of the mixture was adjusted to 1-2. The mixture was stirred for about one hour at 0-5° C. to obtain solid which was filtered and dried under vacuum (11 gms).

ii) To 10 gms (0.02583 moles) of the product obtained from step i) 5% NaOH solution (7 gms of NaOH dissolved in 140 ml of water) was added and heated to about 90° C. till completion of the reaction. The mixture was cooled gradually to 10-15° C. and pH was adjusted to 9-9.5 using 2N HCl. To this solution 3×20 ml of washings were given with EtOAc and the pH was adjusted to 4.5-5 using 2N HCl. The mixture was maintained at 25-30° C. and stirred for about half an hour. The pH of the mixture was maintained at 4.5-5 and extracted with 40 ml of dichloromethane followed by washings with 2×20 ml of dichloromethane. The separated organic layer was concentrated below 45° C. to get a residue. To the residue 70 ml of acetone was added and cooled to 0-5° C. HCl gas was purged through the solution to attain pH of 1-2. The mixture was stirred at 25-30° C. and gradually cooled to 0-5° C. for one hour whereby the solid was obtained. The solid was filtered and dried under vacuum to obtain Levocetirizine (7 gms).

It will be appreciated that the invention may be modified within the scope of the appended claims.

What is claimed is:

1. A process for the preparation of levocetirizine or a salt thereof, which comprises preparing a compound of formula (I)

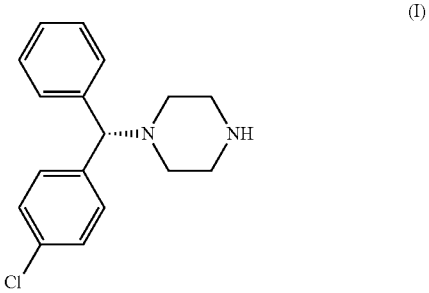 [SMILES: Clc1ccc([C@H](c2ccccc2)N2CCNCC2)cc1]

by reacting a compound of formula (IV) with a deprotecting agent to obtain the corresponding carbamate ester of (−)-1-[(4-chlorophenyl)-phenyl methyl] piperazine, and hydrolysing the carbamate ester to obtain the compound (I), converting the compound (I) to levocetirizine, wherein the compound of formula (IV) has the following structure:

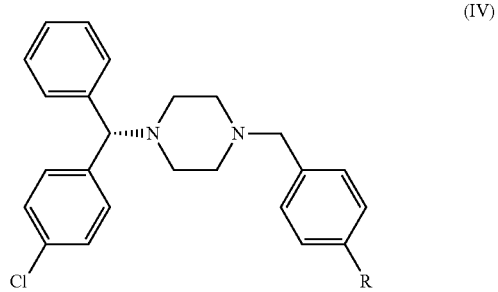

wherein R is Cl, Br, $NO_2$, OH or OR', and R' is alkyl; and
wherein the compound of formula (IV) is prepared by reacting a compound of formula (III) with (−)-(4-chlorophenyl) phenyl methyl amine in the presence of a base and a solvent

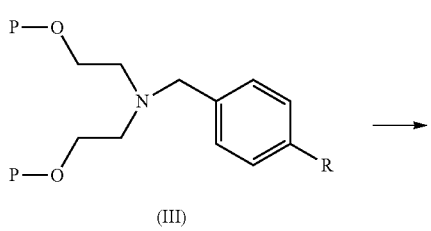

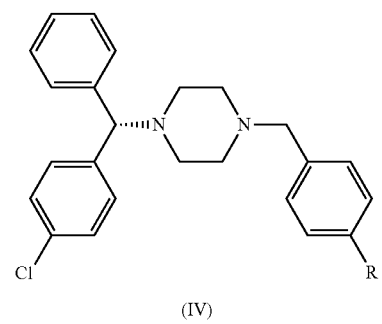

wherein R is Cl, Br, $NO_2$, OH or OR'. and R' is alkyl. and wherein P is a protecting group.

2. The process according to claim 1, wherein the base is selected from potassium carbonate, pyridine, triethyl amine and N,N-diisopropylethyl amine.

3. The process according to claim 1, wherein the solvent is selected from toluene, dimethylsulfoxide, N,N-dimethylformamide, acetonitrile, hexamethyl phosphoramide, N-methyl pyrrolidine, dimethylacetamide, dioxane, sulfolane, tetrahydrofuran and mixtures thereof.

4. The process according to claim 1, wherein the protecting agent is selected from mesylate, besylate, tetrabutyl dimethyl silyl, dimethoxy trityl, tetra isopropyl silyl and tetrahydropyranyl.

5. The process according to claim 1, wherein the deprotecting agent is selected from ethyl chloroformate, 1-chloroethyl chloroformate, vinyl chloroformate, phenyl chloroformate, 2,2,2-trichloroethyl chloroformate, 4-chlorophenyl chlorothionoformate, 2,4,6-tribromophenyl chlorothionoformate, triphosgene and cyanogen bromide.

6. The process according to claim 1, wherein the hydrolysis is carried out using methanol.

7. The process according to claim 1, wherein the conversion of compound (I) to levocetirizine comprises reacting compound (I) with a 2-chloroethoxy acetic acid derivative in the presence of a base and a solvent to obtain the corresponding [2-[4-[(4-chlorophenyl)phenyl methyl]-1-piperazin-1-yl]ethoxy] acetic acid derivative, and hydrolyzing the acetic acid derivative to obtain levocetirizine.

8. The process according to claim 7, wherein the 2-chloroethoxy acetic acid derivative is 2-chloroethoxy acetamide, 2-chloroethoxy acetate or 2-chloroethoxy acetonitrile.

9. The process according to claim 7, wherein the base is sodium carbonate or potassium carbonate.

10. The process according to claim 7, wherein the solvent is toluene or xylene.

11. The process according to claim 7, wherein the hydrolysis is carried out using sodium hydroxide.

12. The process according to claim 1, wherein compound (III) has the following structure (IIIa)

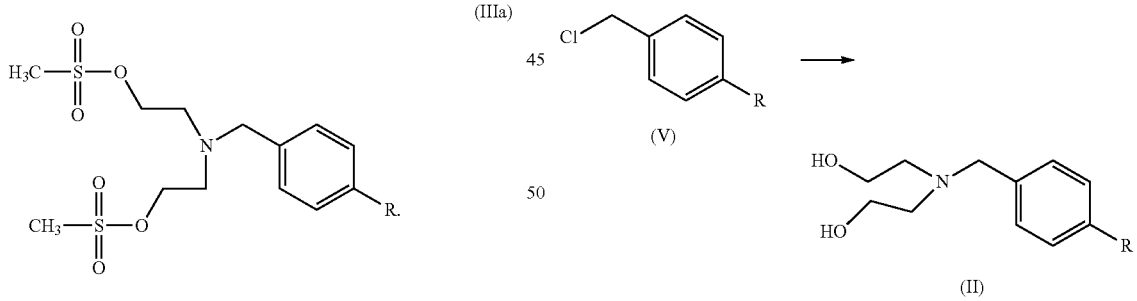

13. The process according to claim 1, further comprising purifying compound (IV).

14. The process according to claim 13, wherein the purification comprises converting compound (IV) to a salt thereof by reaction of compound (IV) with an acid, reacting the salt with a basic solution and isolating compound (IV).

15. The process according to claim 14, wherein the basic solution is a solution of sodium hydroxide solution, and the isolation comprises extraction using a solvent selected from dichloromethane, ethyl acetate and toluene.

16. The process according to claim 1, wherein the compound of formula (III) is prepared by reacting a compound of formula (II) with a protecting agent in the presence of a solvent and a base

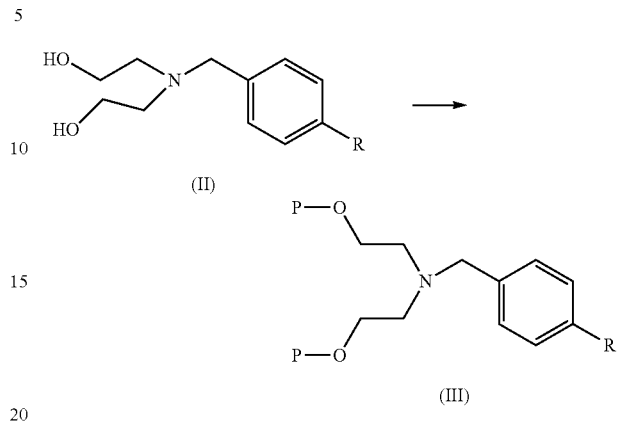

wherein R is Cl, Br, $NO_2$, OH or OR', and R' is alkyl, and wherein P is a protecting group corresponding to the protecting agent.

17. The process according to claim 16, wherein the protecting agent is selected from methane sulfonyl chloride, benzene sulfonic acid, tetrabutyl dimethyl silane, dimethoxy trityl chloride, tetra isopropyl silyl chloride and tetrahydropyran.

18. The process according to claim 16, wherein the protecting group is methane sulfonyl chloride.

19. The process according to claim 16, wherein the base is selected from potassium tertbutoxide, potassium carbonate, sodium methoxide, potassium methoxide, sodium carbonate, pyridine, triethyl amine and N,N-diisopropylethyl amine.

20. The process according to claim 16, wherein the solvent is selected from dichloromethane, acetonitrile, tetrahydrofuran, ethyl acetate and toluene.

21. The process according to claim 16, wherein the compound of formula (II) is prepared by condensation of diethanolamine and a benzyl chloride of formula (V) in the presence of a base and a solvent wherein R is Cl, Br, $NO_2$, OH or OR', and R' is alkyl.

22. The process according to claim 21, wherein the base is selected from potassium tertbutoxide, potassium carbonate, sodium methoxide, potassium methoxide, sodium carbonate, pyridine, triethyl amine and N,N-diisopropylethyl amine.

23. The process according to claim 21, wherein the solvent is selected from dichloromethane, ethyl acetate, toluene, acetone, acetonitrile, tetrahydrofuran and methanol.

* * * * *